(12) United States Patent
Yang et al.

(10) Patent No.: US 8,829,238 B2
(45) Date of Patent: Sep. 9, 2014

(54) METHODS FOR THE SYNTHESIS OF DEUTERATED ACRYLATE SALTS

(75) Inventors: Jun Yang, Oak Ridge, TN (US); Peter V. Bonnesen, Knoxville, TN (US); Kunlun Hong, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 211 days.

(21) Appl. No.: 13/611,927

(22) Filed: Sep. 12, 2012

(65) Prior Publication Data
US 2013/0079554 A1    Mar. 28, 2013

Related U.S. Application Data

(60) Provisional application No. 61/537,710, filed on Sep. 22, 2011.

(51) Int. Cl.
*C07C 51/36* (2006.01)

(52) U.S. Cl.
CPC ............. *C07C 51/36* (2013.01); *C07B 2200/05* (2013.01)
USPC ........................................................ 562/599

(58) Field of Classification Search
CPC ............................ C07C 51/36; C07B 2200/05
USPC ........................................................ 562/599
See application file for complete search history.

(56) References Cited

PUBLICATIONS

Jeon et al, Bull Korean Chem. Soc (2003), 24(12), p. 1845-8.*

* cited by examiner

*Primary Examiner* — Yong Chu
(74) *Attorney, Agent, or Firm* — Scully, Scott, Murphy & Presser, P.C.

(57) ABSTRACT

A method for synthesizing a deuterated acrylate of the Formula (1), the method comprising: (i) deuterating a propiolate compound of Formula (2) to a methyne-deuterated propiolate compound of Formula (3) in the presence of a base and $D_2O$: and (ii) reductively deuterating the methyne-deuterated propiolate compound of Formula (3) in a reaction solvent in the presence of deuterium gas and a palladium-containing catalyst to afford the deuterated acrylate of the Formula (1). The resulting deuterated acrylate compounds, derivatives thereof, and polymers derived therefrom are also described.

26 Claims, No Drawings

US 8,829,238 B2

METHODS FOR THE SYNTHESIS OF DEUTERATED ACRYLATE SALTS

CROSS REFERENCE TO RELATED APPLICATION

This application claims the benefit of priority from U.S. Provisional Application 61/537,710 filed on Sep. 22, 2011.

GOVERNMENT SUPPORT

This invention was made with government support under Prime Contract No. DE-AC05-00OR22725 awarded by the U.S. Department of Energy. The government has certain rights in the invention.

FIELD OF THE INVENTION

The present invention relates, generally, to polymerizable deuterated monomers and methods of preparation, and more particularly, to deuterated acrylate salts and methods of their preparation.

BACKGROUND OF THE INVENTION

Strategic deuteration of macromolecules can be used in combination with nuclear magnetic resonance (NMR), infrared analysis, and neutron-based probing methods, such as small angle neutron scattering (SANS), to obtain rich structural and dynamic information that may be inaccessible by other methods. Such methodology can be particularly important for molecules that do not crystallize, or where understanding of the solution structural and/or dynamic details is required. Acrylic-based macromolecules are ubiquitous in many materials used in daily life, and acrylic polymers with novel properties for new applications are highly sought. In many applications, it is both important yet challenging to elucidate the structure-function relationship for these macromolecules. Techniques such as neutron scattering can provide much insight into this relationship; however, the generally high cost of key monomers such as acrylic acid-$d_3$ ($D_2C=CD-CO_2H$) has been an obstacle for researchers wishing to prepare strategically deuterated acrylic polymers. Although there exist a variety of examples for introducing the vinyl-$d_3$ ($^2H_3$-acrylic) group as a substituent using $D_2CO$ and the Wittig reaction (e.g., P. Keller, et al., *Macromolecules* 35, pp. 581-584, 2002, and J. Pitlik, et al., *J. Labelled Compd. Radiopharm.* 39, pp. 999-1009, 1997), current methods for making deuterated acrylate salts and the corresponding acid, such as $D_2C=CD-CO_2H$ or $D_2C=CD-CO_2D$, are generally complex, costly, and limited to small scale production.

SUMMARY OF THE INVENTION

A convenient and economical method for converting the relatively inexpensive propiolic acid to sodium acrylate-$d_3$, $D_2C=CD-CO_2Na$, a shelf-stable precursor to a wide variety of acrylic-$d_3$ monomers, is herein described. The method provides very good isolated yields (for example, up to 89%, at greater than 95 atom % D), containing only small amounts of sodium propiolate-d ($DC=C-CO_2H$) and sodium propionate-$d_5$ ($CD_3CD_2-CO_2H$). The synthesis uses readily available Lindlar catalyst, which can be conveniently recovered for potential reuse, and the relatively inexpensive deuterated starting materials $D_2$, $D_2O$, and $CH_3OD$. The latter two can also be effectively recovered for potential reuse.

In one aspect, the invention is directed to a method for synthesizing deuterated acrylate compounds. In a further aspect, the invention is directed to a method for preparing a deuterated acrylic acid compound from the deuterated acrylate salt. The invention is also directed to the resulting deuterated acrylate compounds produced by the method, as well as deuterated acrylic acid compounds derived from the deuterated salt.

The invention is particularly directed to a method for the synthesis of a deuterated acrylate compound of the formula:

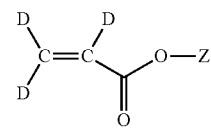

(1)

wherein Z is an alkali metal atom or a hydrogen atom (H), or a deuteron (D), and the line shown between O and Z in Formula (1) is generally indicative of an ionic bond when Z is an alkali metal atom, or the line is indicative of a covalent bond when Z is H.

The method includes a first step of: (i) deuterating a compound of Formula (2) to a compound of Formula (3) by the following reaction pathway conducted in the presence of a base and $D_2O$:

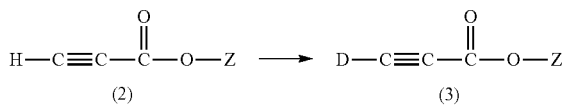

The method includes a second step of: (ii) reductively deuterating the compound of Formula (3) in a reaction solvent in the presence of deuterium gas and a palladium-containing catalyst to afford the deuterated acrylate of the Formula (1).

The method advantageously provides a way to make a deuterated acrylate salt or deuterated acrylic acid in significant yield by a much less costly and more straightforward methodology. The method as applied to the production of deuterated acrylate salt is particularly advantageous in that deuterated acrylic acid, i.e., $D_2C=CD-CO_2H$ or $D_2C=CD-CO_2D$, can be produced therefrom in situ. This is particularly advantageous from the standpoint that, even when stored cold and inhibited, acrylic acid has significant shelf-life limitations. Moreover, other specialty deuterated acrylic monomers can be produced from either the deuterated acrylate salt or acrylic acid. The method described herein is further advantageous by being amenable to significant scale up.

DETAILED DESCRIPTION OF THE INVENTION

As used herein, the term "about" generally indicates within ±0.5%, 1%, 2%, 5%, or up to ±10% of the indicated value. For example, a temperature of about 25° C. generally indicates in its broadest sense 25° C.±10%, which indicates 22.5-27.5° C.

The deuterated acrylate compounds considered herein have the following formula:

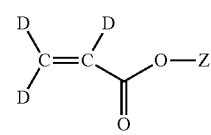

(1)

In Formula (1), Z is an alkali metal atom or hydrogen atom (H) or a deuteron (D). The alkali metal atom can be, for example, lithium (Li), sodium (Na), potassium (K), rubidium (Rb), or cesium (Cs).

The method described herein for synthesizing a compound according to Formula (1) includes at least steps (i) and (ii), as further described below.

The first step, i.e., step (i), includes deuterating a compound of Formula (2) to a compound of Formula (3) by the following reaction pathway conducted in the presence of a base and deuterated water ($D_2O$):

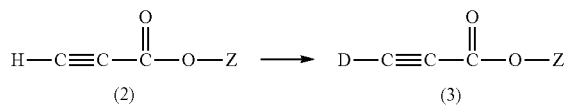

In Formulas (2) and (3) above, Z is as defined above in Formula (1). The base can be any organic or inorganic base, but is preferably a non-protic base. Some examples of organic bases include the alkylamines (e.g., methylamine, ethylamine, n-propylamine, isopropylamine, n-butylamine, isobutylamine, t-butylamine, and cyclohexylamine), the dialkylamines (e.g., dimethylamine, methylethylamine, diethylamine, methylpropylamine, diisopropylamine, methylbutylamine, diisobutylamine, and piperidine), the trialkylamines (e.g., trimethylamine, triethylamine, triisopropylamine), aromatic amines (e.g., aniline, pyridine, and imidazole), ammonium hydroxides (e.g., trimethylammonium hydroxide, triethylammonium hydroxide, and benzyltrimethylammonium hydroxide), alkoxides (e.g., lithium methoxide, sodium methoxide, sodium ethoxide, and lithium isopropoxide), as well as partially and completely deuterated forms of these bases. Some examples of inorganic bases include lithium hydroxide, sodium hydroxide, potassium hydroxide, and the carbonate salts, such as lithium carbonate, sodium carbonate, potassium carbonate, magnesium carbonate, lithium bicarbonate, sodium bicarbonate, and potassium bicarbonate.

The base used in step (i) can be used in any suitable amount or concentration that is an effective amount, i.e., that promotes or facilitates the exchange reaction in step (i). In different embodiments, the base is included in the reaction medium in a concentration of, for example, 1, 2, 5, 10, 20, 30, 40, 50, 100, 150, or 200 mM, or a concentration within a range bounded by any two of these values.

In one embodiment, the reaction solvent used in step (i) is strictly deuterated water ($D_2O$), which is preferably at least or above 95, 96, 97, 98, 99, 99.5, 99.8, or 99.9 atom % D $D_2O$. In other embodiments, the reaction solvent used in step (i) may further include a polar protic or non-protic deuterated solvent, preferably having a boiling point up to or less than 100° C., 80° C., 70° C., or 60° C., such as a deuterated alcohol, such as deuterated methanol (e.g., $CH_3OD$ or $CD_3OD$) or a deuterated ethanol (e.g., $CH_3CH_2OD$). A non-deuterated solvent miscible in water may also be included as long as it does not back exchange (e.g., acetone or acetonitrile). In some embodiments, one or more (or all) solvents other than deuterated water are excluded from the reaction medium.

The exchange process described above in step (i) is conducted for a period of time that permits a sufficient level of proton exchange, preferably the amount of time necessary for equilibration to be reached, after which time the deuterated water is spent and can no longer provide further deuteration. The amount of time that the compound of Formula (2) is incubated with deuterated water can be precisely, about, at least, above, or up to, for example, 0.5, 1, 2, 3, 4, 5, 10, 12, 15, 18, 20, 24, 30, 36, 40, 48, 56, 60, 68, or 72 hours, or a processing time within a range bounded by any of the foregoing exemplary processing times. The reaction time is highly dependent on other process conditions, such as the reaction temperature.

In some embodiments, step (i) is practiced by repeating the exchange process one or more times after the deuterated solvent has been removed. To repeat the exchange process, fresh deuterated water (and optionally, the base and/or any additional solvent) is added to the reaction residue formed in a previous exchange process after spent deuterated water (which includes $D_2O$, and its protonated forms, such as DHO or $H_2O$) from the previous exchange process is partially or completely removed. After fresh deuterated water is added, the second exchange process is conducted under conditions, as described above for the first exchange process, that promotes proton-deuteron exchange with the propiolate compound of Formula (2). A third exchange process can be conducted, if desired, by removing the spent deuterated water used in the second exchange process, adding fresh deuterated water, and conducting the third exchange process under conditions that promote proton-deuteron exchange, as above. A fourth or higher number of exchange processes can be used by repeating the process. Each exchange process is herein also referred to as a "contact". The number of contacts, which includes the first exchange process, can be, for example, one, two, three, four, or a higher number of contacts.

With each contact, the extent (level) of deuteration (atom % D) generally increases. Typically, after the first contact, the deuterated propiolate compound of Formula (3) has a level of deuteration of at least 80, 85, 90, 92, 95, or 97 atom % D; after a second contact, the deuterated propiolate compound of Formula (3) typically has a level of deuteration of at least 85, 90, 92, 95, 97, 98, or 99 atom % D; and after a third contact, the deuterated propiolate compound of Formula (3) typically has a level of deuteration of at least 90, 92, 95, 97, 98, 99, 99.5, or 99.7 atom % D.

The process of step (i) can be conducted at any suitable temperature. Typically, step (i) is conducted at room temperature, which can be considered a temperature of about 18, 20, 25, or 30° C. In other embodiments, step (i) is conducted above room temperature and up to 100° C., such as a temperature of precisely, about, or at least 40° C., 50° C., 60° C., 70° C., 80° C., or 90° C. In yet other embodiments, step (i) is conducted at a temperature above 100° C., along with suitable pressurization, but below the critical temperature of water, i.e., less than 374° C., or below a decomposition temperature of the propiolate compound of Formula (2) or (3). The processing temperature may be precisely, about, up to, or less than, for example, 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., or 350° C., or a temperature within a range bounded by any two of the foregoing exemplary temperatures. It is understood that higher temperatures generally require a shorter period of time to bring the reaction to completion.

Typically, the process of step (i) is conducted at standard atmospheric pressure, i.e., about 1 atm, or about 14.7 psi. However, in some embodiments, the process of step (i) may be conducted at a pressure above 1 atm. The elevated pressure may be precisely, about, at least, above, up to, or less than, for example, 1, 2, 3, 4, 5, 6, 7, 8, 9, 10, 15, 20, 30, 40, 50, 60, 70, 80, 90, 100, 125, 150, 175, or 200 atm, or a pressure within a range bounded by any two of the foregoing exemplary pressures. In other terms, the pressure can be precisely, about, at least, above, up to, or less than, for example, 15, 20, 50, 70, 100, 120, 130, 140, 150, 160, 170, 180, 200, 250, 300, 350, 400, 450, 500, 550, 600, 700, 800, 900, 1000, 1500, 2000, 2500, or 3000 psi, or a pressure within a range bounded by any two of the foregoing exemplary pressures. The pressure is generally below the critical pressure of water, i.e., less than 218 atm (approximately 3200 psi). In some embodiments, a reduced pressure may be used, such as a pressure of less than 1 atm, or a pressure of precisely, about, up to, or less than, for example, 0.5, 0.2, or 0.1 atm.

The intermediate of Formula (3) is preferably obtained in a yield of at least 70%, as calculated from the starting compound of Formula (2). In different embodiments, the yield of the intermediate of Formula (3) is at least or above 70%, 75%, 80%, 85%, 90%, 95%, 97%, 98%, 99%, or in quantitative yield (i.e., about or precisely 100%). Moreover, the ratio of intermediate compound of Formula (3) produced in step (i) to non-deuterated starting material (i.e., compound of Formula 2) is preferably at least 80:20 and up to or at least, for example, 85:15, 90:10, 95:5, 97:3, 98:2, 99:1, or 100:0. The foregoing ratios may alternatively be stated as a selectivity value (mole ratio of desired product over total product×100), such as a selectivity of 85, 90, 95, 97, 98, 99, or 100%, respectively.

Once a sufficiently deuterated form of the intermediate of Formula (3) is achieved, solvent is substantially or completely removed (e.g., by vacuum distillation). In preferred embodiments, the product of step (i) is dried, i.e., made to be substantially or completely bereft of water (e.g., by subjecting to high vacuum), before being used in step (ii). The product of step (i), once initially removed of solvent, may be further purified from remaining base and salt byproduct according to any of the techniques well known in the art. For example, the product of step (i) may be washed with an organic solvent (such as diethyl ether) in which it is mostly insoluble, but that reaction byproducts (i.e., organic bases) are soluble. Alternatively, the product of step (i) may be extracted into an organic solvent that does not undo the deuteration achieved in step (i) and which preferably dissolves the deuterated product of Formula (3) and not reaction byproducts (i.e., base and/or salts). In the latter case, the organic solvent holding the product may optionally be dried with a drying agent, and the volatile portion of the organic phase removed by evaporation to provide an initially or finally isolated product of step (i) according to Formula (3). If desired, the initially isolated product of step (i) may be crystallized, recrystallized, or otherwise purified by techniques well known in the art, before being used in the reaction of step (ii).

In step (ii), the compound of Formula (3) is reductively deuterated in a reaction solvent in the presence of deuterium gas ($D_2$) and a palladium-containing catalyst to afford the deuterated acrylate of Formula (1). The general reaction scheme is as follows:

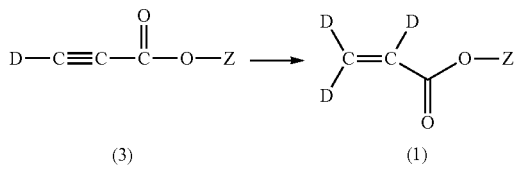

The reaction solvent for the reaction of step (ii) is preferably a protic deuterated organic solvent in which compound of Formula (3) is mostly or completely soluble, such as deuterated methanol or ethanol, wherein the deuterated alcohol is at least deuterated at the protic hydrogen atom. In particular embodiments, the reaction solvent is deuterated methanol, which may be, for example, $CH_3OD$ or $CD_3OD$. In some embodiments, the reaction solvent may be non-protic and polar, and may be deuterated or non-deuterated, and preferably a lower boiling solvent (i.e., a b.p. of up to or less than 100° C., 80° C., 70° C., or 60° C.), such as acetone, 1,2-dimethoxyethane (DME), or acetonitrile. A mixture of such solvents may also be used. The reaction solvent may or may not include a base, such as sodium carbonate or bicarbonate. In some embodiments, the reaction solvent excludes water, deuterated water, an aqueous basic solution (particularly, aqueous sodium hydroxide), a protic solvent not deuterated at the protic hydrogen atom, or a non-deuterated protic solvent.

In some embodiments, the deuterium gas used in step (ii) is the sole atmospheric gas for the reaction. However, in preferred embodiments, the deuterium gas is admixed with an inert gas, such as nitrogen gas ($N_2$) or a noble gas (e.g., helium or argon), preferably at an atmospheric pressure of about 1 atm. In some embodiments, the deuterium gas is used in a molar amount within 10% of or precisely at the stoichiometric amount necessary for reaction. In other embodiments, the deuterium gas is used in an excess molar amount. The excess molar amount can be, for example, 1, 2, 5, 7, 10, 12, 15, 18, or 20% excess. The reaction of step (ii) is preferably conducted in the substantial or complete absence of oxygen. Oxygen can be substantially minimized or excluded from the reaction by, for example, purging the reaction vessel with an inert gas before or during the reaction.

The palladium-containing catalyst (i.e., "catalyst") used in step (ii) is any homogeneous or heterogeneous palladium-containing catalyst that can effect a reductive hydrogenation (in this case, deuteration) of an alkyne to an alkene in the presence of hydrogen gas (in this case, deuterium gas). Typically, the palladium in the catalyst is in the form of zerovalent palladium, i.e., Pd(0). For the purposes of the instant invention, the catalyst should be capable of reducing the alkyne (C—C triple bond) to the alkene (C—C double bond) in the substantial absence of saturated product (i.e., alkane, or C—C single bond) and other undesirable byproducts (e.g., oligomers) under appropriate conditions. In some embodiments, the palladium-containing catalyst may include one or more other metals that may serve, for example, to favorably augment, modify, promote, or optimize the catalytic properties of the catalyst. The additional metal may be, for example, another noble metal, such as platinum, gold, silver, rhodium, or iridium. Some other catalytically active transition metals include iron, cobalt, nickel, molybdenum, ruthenium, rhenium, and tungsten. In other embodiments, one or more of the foregoing classes or specific kinds of metals other than palladium are excluded from the catalyst, or the palladium-containing catalyst described herein may contain only palladium as a metal.

The catalyst is included in the reaction of step (ii) in an effective amount by weight of the compound of Formula (3). The catalyst can be used in an amount of, for example, 1, 2, 3, 4, 5, 6, 7, 8, 10, 12, 15, 20, 25, or 30 wt % by weight of the compound of Formula (3), or an amount within a range bounded by any two of the foregoing exemplary values.

In some embodiments, the catalyst includes a support, typically an inorganic support. Some examples of support materials include alumina, silica, titania, zirconia, calcium carbonate, calcium sulfate, barium sulfate, carbon, and zeolites. The palladium can be included on the support in any suitable amount, such as precisely, about, at least, above, up to, or less than, for example, 1, 2, 3, 4, 5, 6, 7, 8, 9, 10, 12, 15, 18, or 20 wt % by weight of the support and palladium. In other embodiments, the catalyst is not on a support, such as a soluble metal complex, which may be a metal-ligand complex, wherein the ligand can be, for example, a monodentate, bidentate, tridentate, tetradentate, pentadentate, or hexadentate ligand. The ligand preferably does not have a deleterious impact on the palladium catalyst or other aspects of the reaction. In yet other embodiments, the catalyst is in the form of colloidal palladium, such as a polyethylene imine-Pd catalyst, as described in Mori, S., et al., *J. Mol. Catal. A: Chem.,* 2009, 307, pp. 77-87 or Sajiki, H., et al., *Chem.-Eur. J.,* 2008, 14(17), pp. 5109-5111.

In particular embodiments, the palladium-containing catalyst is a Lindlar catalyst, which encompasses all of the known types and variations of Lindlar catalysts of the art. Typically, the Lindlar catalyst includes zerovalent palladium on a support, typically calcium carbonate or barium sulfate. The Lindlar catalyst also typically includes one or more deactivators, i.e., "catalytic poisons", either as a component of the catalyst or included in the reaction solution, that lessen or favorably augment the catalytic activity of the catalyst to substantially or completely prevent the production of undesired product, such as completely saturated product or oligomers.

Typically, the Lindlar catalyst includes a lead additive as a catalyst poison. The lead additive can be, for example, lead carbonate, lead acetate, or lead oxide. The lead additive can be included in an amount of, for example, 1, 2, 3, 4, 5, 6, 7, 8, 9, 10, 11, or 12 wt % by total weight of the catalyst (generally, only considering palladium, the lead additive, and support in the total weight of the catalyst), or in an amount within a range bounded by any of the foregoing exemplary values.

The Lindlar catalyst also typically includes an organic inhibitor, which can be any organic compound that includes one or more heteroatoms capable of binding to a metal, particularly palladium. The heteroatoms are typically selected from nitrogen and sulfur. As used herein, the term "organic compound" refers to a compound that includes at least one carbon atom, and typically, at least one carbon-hydrogen and/or carbon-carbon bond. In one set of embodiments, the organic inhibitor is a heterocyclic compound, which may be a monocyclic, bicyclic, tricyclic, or higher cyclic compound, and either saturated or unsaturated (e.g., aliphatic or aromatic). Some examples of nitrogen-containing heterocyclic compounds include quinoline, indole, quinazoline, quinoxaline, pyrrole, imidazole, pyrazole, pyridine, bipyridine, oxazole, purine, pyrimidine, pyrazine, piperidine, and piperazine, including alkyl-substituted derivatives thereof, such as 4-methylquinoline or 8-methylquinoline. Some examples of sulfur-containing heterocyclic compounds include thiophene, thiazole, and thiomorpholine. Quinoline is a particularly common organic inhibitor for use in Lindlar catalysts. In another set of embodiments, the organic inhibitor is a cyclic, straight-chained, or branched hydrocarbon substituted with one or more nitrogen and/or sulfur heteroatoms. Some examples of nitrogen-containing hydrocarbons include ethylenediamine, diethylenetriamine, ethanolamine, tris(2-aminoethyl)amine, and aniline. Some examples of sulfur-containing hydrocarbons include the thiols (e.g., thiophenol, thiocresol, monothioethyleneglycol, and dithioethyleneglycol), thioethers (e.g., thiodiethyleneglycol and cyclic thioethers). In particular embodiments, the sulfur-containing organic inhibitor is 2,2'-(ethylenedithio)diethanol. A comprehensive description of organic sulfur compounds useful as inhibitors is found in U.S. Pat. No. 3,715,404, which is incorporated herein by reference in its entirety. In some embodiments, any one or more of the foregoing classes or specific types of organic inhibitors are excluded from the catalyst or the reaction process of step (ii).

The organic inhibitor can be included in any suitable amount at which the inhibitor effectively or optimally inhibits the catalyst. The organic inhibitor may either be incorporated into the catalyst at the start of the reaction, or the organic inhibitor may be added to the reaction medium at the start of or during the reaction. In different embodiments, the organic inhibitor is included in an amount of precisely, about, at least, above, up to, or less than, for example, 1, 2, 5, 10, 15, 20, 25, 30, 35, 40, 45, 50, 60, 70, 80, 90, 100, 150, 200, 250, 300, 400, 500, 600, 700, 800, 900, or 1000 wt % by weight of the catalyst (generally, only considering palladium, the lead additive, and support in the total weight of the catalyst), or in an amount within a range bounded by any of the foregoing exemplary values. In particular embodiments, the organic inhibitor is included in an amount of precisely, about, up to, or less than 1, 2, 5, 10, 15, 20, 25, 30, 35, 40, 45, or 50 wt % by weight of the catalyst.

The lead additive is often used in combination with an organic inhibitor; however, in some embodiments, the lead additive is used in the absence of an organic inhibitor. Similarly, the organic inhibitor is typically used in combination with a lead additive; however, the organic inhibitor may be used without a lead additive or may be included in combination with another type of catalyst poison.

In some embodiments, the reaction process of step (ii) further includes a radical polymerization inhibitor. The radical polymerization inhibitor can be any such compounds known in the art, such as, for example, hydroquinone, the quinones (e.g., 1,4-benzoquinone, 1,2-benzoquinone, 1,4-naphthoquinone, 9,10-anthraquinone, tetrachloro-α-benzoquinone, and dichlorodicyanobenzoquinone), the substituted phenols (e.g., 4-methylphenol or 4-t-butylphenol), catechol and substituted catechols (e.g., 4-t-butylcatechol), or a hydroxytoluene, particularly the alkylated hydroxytoluenes, such as 2,6-di-tert-butyl-4-methylphenol, also known as butylated hydroxytoluene or BHT. In some embodiments, any one or more of the foregoing classes or specific types of radical polymerization inhibitors may be excluded from the catalyst or entire process of step (ii). The radical polymerization inhibitor can be included in an amount of precisely, about, up to, or less than, for example, 0.1, 0.2, 0.5, 1, 2, 3, 4, or 5 wt % by weight of the compound of Formula (3).

The reductive hydrogenation reaction described above in step (ii) is conducted for a period of time (reaction time) until no further consumption of deuterium gas is observed, or until deuterium gas is completely consumed. The amount of time for the reaction to reach completion can be precisely, about, at least, above, or up to, for example, 0.5, 1, 2, 3, 4, 5, 6, 7, 8, 10, 12, 15, 18, 20, 24, 30, 36, 40, 48, 72, 96, or 120 hours, or a reaction time within a range bounded by any of the foregoing exemplary processing times. The reaction time is highly dependent on other process conditions, such as the reaction temperature.

The process of step (ii) can be conducted at any suitable temperature. Typically, step (ii) is conducted at room temperature, which can be considered a temperature of about 18, 20, 25, or 30° C. In other embodiments, step (ii) is conducted at an elevated temperature above room temperature and up to the boiling point of the solvent being used, or up to or below a decomposition temperature of the product or the catalyst, either at standard atmospheric pressure or an elevated pressure. The elevated temperature may be, for example, precisely, about, at least, above, up to, or less than, for example, 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., 300° C., 310° C., 320° C., 330° C., 340° C., or 350° C., or a temperature within a range bounded by any two of the foregoing exemplary temperatures. It is understood that higher temperatures generally require a shorter period of time to bring the reaction to completion. In other embodiments, step (ii) is conducted at a temperature below room temperature and down to the freezing (melting) point of the solvent being used, either at standard atmospheric pressure or an elevated or reduced pressure. The lower temperature may be, for example, precisely, about, at least, above, up to, or less than, for example, 15° C., 10° C., 5° C., 0° C., −5° C., −10° C., −15° C., −20° C., −25° C., or −30° C. Although lower temperatures generally require a longer period of time to bring the reaction to completion, in some embodiments a lower temperature may provide an advantage in controlling the reactivity of the catalyst and thereby enhancing the selectivity.

Typically, the process of step (ii) is conducted at standard atmospheric pressure, i.e., about 1 atm, or about 14.7 psi. However, in some embodiments, the process of step (ii) may be conducted at a pressure above 1 atm. The elevated pressure may be precisely, about, at least, above, or up to, for example, 2, 3, 4, 5, 6, 7, 8, 9, 10, 15, 20, 30, 40, 50, 60, 70, 80, 90, 100, 125, 150, 175, or 200 atm, or a pressure within a range bounded by any two of the foregoing exemplary pressures. In other terms, the pressure can be precisely, about, at least, above, or up to, for example, 15, 20, 50, 70, 100, 120, 130, 140, 150, 160, 170, 180, 200, 250, 300, 350, 400, 450, 500, 550, 600, 700, 800, 900, 1000, 1500, 2000, 2500, or 3000 psi, or a pressure up to a critical pressure of the reaction solvent used, or a pressure within a range bounded by any two of the foregoing exemplary pressures. In some embodiments, a reduced pressure may be used, such as a pressure of less than 1 atm, or a pressure of precisely, about, up to, or less than, for example, 0.5, 0.2, or 0.1 atm.

The product of step (ii) can be isolated and purified by any means known in the art. As an initial matter, the product of step (ii) is normally separated from the catalyst by filtration. In order to filter off the catalyst, the catalyst is either insoluble in the reaction medium, or the catalyst can be made to become insoluble by addition of a non-polar solvent (e.g., diethyl ether) and/or cooling the temperature and/or adding a flocculant. Once initially separated from the catalyst, the product of step (ii) may be purified according to any of the techniques well known in the art. For example, the product of step (ii) may be washed with a non-polar organic solvent (e.g., diethyl ether, tetrahydrofuran, or hexanes) that selectively dissolves one or more reaction byproducts and not the deuterated product of Formula (1). The initially purified product of Formula (1) may optionally be dried, such as by vacuum. If desired, the initially purified product of Formula (1) may be crystallized, recrystallized, or otherwise purified by techniques well known in the art.

The compound of Formula (1) is preferably obtained in a yield of at least 70%, as calculated from the starting compound of Formula (2). In different embodiments, the yield of the compound of Formula (1) is at least or above 70%, 75%, 80%, 85%, 90%, 95%, 97%, 98%, 99%, or in quantitative yield (i.e., about or precisely 100%). Moreover, the ratio of unreacted starting material (i.e., compound of Formula 3) to product of Formula (1) to over-reduced (i.e., over-hydrogenated to saturated propionate) byproduct in step (ii) is preferably at least x:80:(20−x) and up to, for example, x:85:(15−x), x:90:(10−x), x:95:(5−x), x:97:(3−x), x:98:(2−x), or x:99:(1−x), wherein x can be 0, or a number above 0, such as 1, 2, 3, 4, 5, 10, 15, or 20, or within a range therein, provided that x is not greater than the number from which it is being subtracted. In some embodiments, unreacted starting material (i.e., compound of Formula 3) and over-reduced (saturated) product are present in a combined amount of no more than 20, 15, 10, 8, 7, 6, 5, 4, 3, 2, or 1 mole %. Preferably, the product of Formula (1) has a level of deuteration of at least 80, 85, 90, 92, 95, 97, 98, 99, or 99.5 atom % D.

In another aspect, the invention is directed to a process of converting the salt form of the compound of Formula (1), i.e., when Z is an alkali metal atom, to the protonated or deuterated (i.e., acidic) from, i.e., when Z is H or D. The protonation or deuteration reaction can be conducted by methods well known in the art. By methods well known in the art, an acid (e.g., an inorganic or organic acid) with suitable acid strength can be contacted with the salt form of the compound of Formula (1), in the presence of a free-radical polymerization inhibitor, such as hydroquinone, to afford the acidic (protonated) form of the compound of Formula (1). The acid can be, for example, a mineral acid (e.g., HCl, HBr, $HNO_3$, $H_3PO_4$, or $H_2SO_4$, or deuterated analogs as appropriate) or an organic acid (e.g., a carboxylic acid, such as acetic acid or acetic acid-d). The reaction is typically conducted in aqueous solution. As the protonated form of the compound of Formula (1) is more hydrophobic than the corresponding salt form, the protonated form can be separated from the aqueous solution by extracting the aqueous solution with a water-immiscible solvent in which the protonated form of the compound of Formula (1) is soluble, such as diethyl ether, ethyl acetate, chloroform, or methylene chloride. The solvent layer can then be dried before removing the organic solvent. The resulting protonated form of Formula (1) can have any of the level of deuteration and selectivity ratios described above for the salt form of Formula (1).

The invention is also directed to the preparation of any of a variety of acrylate monomer derivatives derivable from the product of Formula (1), particularly by replacement of Z. In particular, by methods well known in the art, the group Z, which may be an alkali metal, or hydrogen atom, or deuterium atom, may be replaced with any of a variety of cationic species that may not be an alkali metal, hydrogen atom, or deuterium atom. The cationic species can be, for example, an alkaline earth metal (e.g., Mg or Ca), an inorganic non-metal species (e.g., $NH_4^+$), or an organic cationic species, such as a quaternary ammonium species (e.g., tetramethylammonium, tetraethylammonium, or butyltrimethylammonium), heterocyclic species (e.g., pyridinium or piperidinium), or quaternary phosphonium species (e.g., tetramethylphosphonium or tetraphenylphosphonium).

The invention is furthermore directed to the polymerization of the product of Formula (1) or a derivative thereof in the preparation of polyacrylate and polyacrylic acid polymers and co-polymers. Methods for the preparation of polyacrylate or polyacrylic acid polymers from acrylate or acrylic acid monomers are well established, and all such methods are considered herein. Some of the methods for polymerizing acrylate or acrylic acid monomers include, for example, free radical polymerization (FRP), anionic polymerization (AP), and controlled radical polymerization (CRP). Some more specific types of CRP include, for example, atom transfer radical polymerization (ATRP), degenerative transfer, reversible fragmentation chain transfer, and nitroxide-mediated polymerization. For the synthesis of a copolymer of acrylate or acrylic acid, the comonomer may be any suitable vinylic compound, which can be non-deuterated, partially deuterated, or completely deuterated, such as, for example, ethylene, propylene, isoprene, styrene, acrylamide, vinylpyridine, an acrylate ester (e.g., methyl acrylate, ethyl acrylate, or butyl acrylate), methacrylic acid, a methacrylate ester (e.g., methyl methacrylate or ethyl methacrylate), acrylonitrile, or butadiene, or a combination thereof. The resulting polyacrylate or polyacrylic acid polymers or copolymers can be directed to any of a variety of applications, including as paints, coatings, textiles, absorbent materials, dispersion media, ion exchange materials, and elastomers.

Examples have been set forth below for the purpose of illustration and to describe certain specific embodiments of the invention. However, the scope of this invention is not to be in any way limited by the examples set forth herein.

EXAMPLE 1

Preparation of Sodium Propiolate by Exchange Reaction of Step (i)

The general reaction scheme for step (i) is provided as follows:

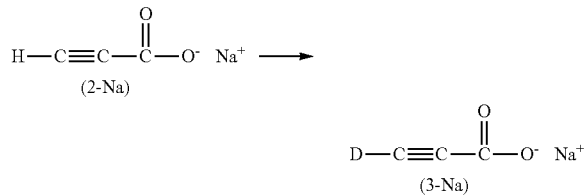

Step (i) involves exchanging the weakly acidic methyne proton with a deuteron by two or three successive contacts of about 1 g of sodium propiolate dissolved in about 1.5-2.2 g of deuterium oxide (at least 1.5 g $D_2O$ is needed to conveniently dissolve 1 g of sodium propiolate). A small amount of the base sodium carbonate (10 mM in the deuterium oxide for the first contact) was herein found to facilitate the H/D exchange. Other bases, such as sodium hydroxide, potassium hydroxide, and potassium carbonate can be used, but the non-protic carbonate bases are preferred, and sodium carbonate is most preferred. After equilibrium is achieved, the $DHO/D_2O$ mixture can be recovered by vacuum distillation (such as by rotary evaporation), and fresh $D_2O$ added to the solids that remain, which includes the sodium carbonate. Typically, for two contacts with 2.2 g $D_2O$ per g of sodium propiolate, 92+ atom % D was achieved on the first contact, and 97+ atom % D was achieved on the second contact. For three contacts with 1.5 g $D_2O$ per g of sodium propiolate, 88+ atom % D was achieved on the first contact, 96+ atom % D was achieved on the second contact, and 99 atom % D was achieved on the third contact.

Preparation of Sodium Propiolate (2-Na)

Sodium propiolate (2-Na) can be conveniently prepared in nearly quantitative yield by treating propiolic acid with sodium hydroxide in methanol (J. D. Jaufmann, et al., *J. Solid State. Chem.* 2000, 152, 99-104); however, sodium propiolate is somewhat light sensitive, and thus, the reaction and product isolation should be conducted using appropriate safeguards to avoid light decomposition. In a darkened hood, ground sodium hydroxide (8.565 g, 0.214 mol) was dissolved in 1 L of methanol in a 2 L round bottom flask. The solution was cooled to 10° C., and propiolic acid (15.0 g, 0.214 mol) was added with stirring. The solution was stirred for 1 hour at room temperature after which the solvent was removed by rotary evaporation at a water bath temperature of ≤25° C. A white solid product, which was dried under high vacuum, was obtained (19.50 g, 99%). The compound was light sensitive, and thus, stored in the dark. $^1H$ NMR ($CD_3OD$): δ 3.36; $^{13}C$ NMR ($CD_3OD$): δ 160.8 (C=O), 81.8 (H—C≡C), 69.3 (H—C≡C).

Preparation of Sodium Propiolate-d (3-Na) Using Two Contacts

In a typical procedure, 10.01 g (108.8 mmol) of sodium propiolate was dissolved under nitrogen in a solution of 10 mM sodium carbonate in 99.9 atom % D $D_2O$ (21.85 g, 1.09 mol $D_2O$), in a 100-mL round bottom flask with a Teflon-coated stir bar. The solution was stirred at room temperature stoppered under nitrogen overnight, after which a 660 microliter sample was withdrawn for analysis by proton and carbon NMR. $^{13}C\{^1H\}$ NMR with no NOE revealed a 92.2:7.8 ratio of the D-CC triplet ($J_{2CD}$=7.3 Hz) to the H—CC singlet from the non-deuterated starting material. The NMR sample was returned to the reaction flask and the $D_2O$ was removed and recovered by vacuum distillation. To the residue was added 21.54 g (1.08 mol) of fresh $D_2O$/sodium carbonate solution and stirring resumed for several days stoppered under nitrogen at room temperature. Alternatively, fresh $D_2O$ with no sodium carbonate could be used here, and only overnight stirring is needed. Analysis of a 660 microliter sample by $^{13}C\{^1H\}$ NMR with no NOE revealed a 97.4:2.6 ratio of deuterated to non-deuterated product. The $D_2O$ was removed and recovered by vacuum distillation, and a few mL of $CH_3OD$ were added and then evaporated to further dry the salt. The yield of the light tan powder so obtained was 9.83 g (97%), and this yield does not include the NMR sample that has the remaining material, so the yield is essentially quantitative. $^{13}C\{^1H\}$ NMR ($D_2O$): δ 160.2 (s, C=O, both deuterated and non-deuterated), 79.5 (s, carbon from residual H—CC), 79.1 ("t", D-CC, $J_{2CD}$=7.7 Hz), 71.1 (s, carbon from residual H—CC), 70.8 ("t", D-CC, $J_{CD}$=39.5 Hz).

Preparation of Sodium Propiolate-d (3-Na) Using Three Contacts

In a typical procedure, sodium propiolate (2-Na, 13.81 g, 0.150 mol) was dissolved under nitrogen in a solution of 10 mM sodium carbonate in 99.9 atom % D $D_2O$ (21.04 g, 1.05 mol $D_2O$) in a 200-mL round bottom flask with a Teflon-coated stir bar. The solution was stirred at room temperature under nitrogen for about 24 hours, at which time a 650 microliter sample was withdrawn for analysis by proton and carbon NMR. $^{13}C\{^1H\}$ NMR with no NOE revealed a 88.7:11.3 ratio of the D-CC triplet ($J_{2CD}$=7.3 Hz) to the H—CC singlet from the non-deuterated starting material. The NMR sample was returned to the reaction flask and the $D_2O$ was removed and recovered by vacuum distillation. To the solid residue that remained was added 21.04 g (1.05 mol) of fresh 99.9 atom % D $D_2O$ (without sodium carbonate, because the initial amount was still present in the flask). Stirring was resumed under nitrogen at room temperature for about 24 hours. Analysis of a 650 microliter sample by $^{13}C\{^1H\}$ NMR with no NOE revealed a 96.8:3.2 ratio of deuterated to non-deuterated product. The NMR sample was returned to the flask, whereafter the procedure was repeated a third time by distilling off the existing $D_2O$/DHO and replacing with 21.04 g of fresh 99.9 atom % D $D_2O$. Analysis by $^{13}C\{^1H\}$ NMR with no NOE revealed a 99.0:1.0 ratio of deuterated to non-deuterated product. The NMR sample was returned to the flask and the $D_2O$ again recovered by vacuum distillation. A few mL of $CH_3OD$ was added and then evaporated to further dry the salt, which was then dried under high vacuum. The yield of the white powder so obtained was 13.84 g (99%). $^{13}C\{^1H\}$ NMR ($D_2O$, TSP): δ 163.0 (s, C=O, both deuterated and non-deuterated), 81.8 (s, carbon from residual 81.3 (t, $J_{2CD}$=7.3

Hz), 73.5 (s, carbon from residual H—C≡C), 73.2 (t, D-C≡C, $J_{CD}$=39.0 Hz); $^2$H NMR (D$_2$O): δ 3.08 (br. s, DC≡C—CO$_2$Na).

EXAMPLE 2

Preparation of Sodium Acrylate by Reductive Hydrogenation Process of Step (ii)

The general reaction scheme is provided as follows:

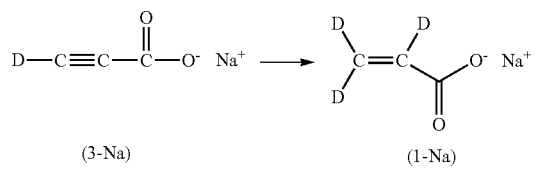 [SMILES: [2H]C#CC(=O)[O-] ; [Na+] ; [2H]C([2H])=C([2H])C(=O)[O-] ; [Na+]]

(3-Na)　　　　　　　　(1-Na)

General Method

In the second step, the alkyne group of sodium propiolate-d is partially reduced to an alkene group using deuterium gas to afford sodium acrylate-d$_3$ (D$_2$C=CD-CO$_2$Na). Although the catalyst system used for this transformation is the well-known Lindlar catalyst (5 wt % Pd(0) supported on calcium carbonate or barium sulfate with usually 3 wt % of lead carbonate of lead sulfate) in combination with the organic base quinoline, it has herein been discovered that there is a narrow set of reaction conditions that can be used to afford the desired D$_2$C=CD-CO$_2$Na product in a facile manner in high yield, and without excessive over-reduction to sodium propionate-d$_5$, CD$_3$CD$_2$-CO$_2$Na.

The main variables in the reductive deuteration reaction include: a) the quality and concentration of the Lindlar catalyst, b) the concentration of deuterium gas and whether a carrier gas such as nitrogen is used, c) the concentration of quinoline used, and d) the nature of the reaction solvent and the concentration of sodium propiolate in the reaction solvent. The activity and selectivity of the Lindlar catalyst can vary depending on its preparation, including how the lead used to "poison" the catalytically active palladium is incorporated. Lindlar catalysts from three different vendors were tested and showed overall similar results with variance in product yields of ±3%. Scoping experiments with both hydrogen and deuterium revealed that use of a blanketing or carrier gas at about 1 atm allows the stoichiometric amount (or a slight excess) of hydrogen or deuterium to be added as a reagent, and that upon consumption, no vacuum is created. In the situation in which the reaction vessel is evacuated, and the hydrogen or deuterium directly added, if a stoichiometric amount of hydrogen or deuterium is used, the reaction becomes starved toward the end, which limits conversion. If an excess amount of hydrogen or deuterium is used to aid in conversion, more over-reduction is observed. Thus, placing the reaction vessel under nitrogen at 1 atm provides a good conversion with minimal over-reduction when stoichiometric or up to 10% excess hydrogen or deuterium is added.

Quinoline can be added to the reaction at anywhere from 0.05× (5%) to 10× (1000%) based on the weight of the catalyst to further enhance selectivity (reduction of only the alkyne and not the alkene) by, it is believed, decreasing surface interactions of the alkene with the catalyst, and hence retarding reduction of the alkene. As the reaction proceeds, and the starting alkyne is reduced to the alkene, the alkyne concentration decreases and the alkene concentration increases, and competition for hydrogen between the desired alkene product and the starting alkyne increases. Maintaining reaction conditions to retard reaction between hydrogen and the alkene (here the desired sodium acrylate) to give the alkane (sodium propionate) becomes increasingly important toward the end of the reaction, particularly when the [alkene]:[alkyne] ratio surpasses 9:1 (90% conversion). However, high concentrations of quinoline also slow the reaction rate, and can lead to incomplete conversion. Moreover, with higher amounts of quinoline, the solid sodium acrylate needs to be extensively washed (e.g., with ether) to completely remove it, and for this reason, a lower level of quinoline is preferred. For example, 0.05× to 0.5× (5-50%) quinoline based on the weight of the catalyst can be a preferred amount to achieve a satisfactory balance of good kinetics and conversion with minimal over-reduction, along with adequate removal from the product.

Finally, the selection of the reaction solvent is very important. Sodium propiolate and sodium acrylate are both soluble in water, and to a lesser extent methanol. Scoping experiments using hydrogen to reduce sodium propiolate to sodium acrylate revealed that the reduction did not proceed properly (almost no reaction) when the solvent was water, dilute (0.05 M) aqueous sodium hydroxide, or a 1:1 mixture of (0.05 M) aqueous sodium hydroxide and methanol. The hydrogenation reaction was greatly improved in methanol. However, when using methanol, it was herein found to be very important to use methanol-d (i.e., CH$_3$OD). If CH$_3$OH is used for the deuteration reaction, back-exchange of the alkyne deuteron of sodium propiolate-d with the methanol proton occurs during the reaction, which results in a product mixture of both deuterated and protonated (non-deuterated) sodium acrylate. Methanol-d is also advantageously inexpensive and in good supply. Also, the Lindlar catalyst can be easily filtered away from the methanol reaction mixture, and the methanol-d easily recovered by distillation/rotary evaporation for reuse.

Survey Reactions with Hydrogen

Prior to conducting reactions using deuterium, a series of survey reactions were herein performed using hydrogen gas to determine the optimum reaction conditions that would maximize the yield of non-deuterated sodium acrylate (4), while minimizing the amount of sodium propiolate (2-Na) remaining and the amount of sodium propionate (5) produced. Experimental details are provided below.

In a typical procedure, a 250-mL round bottom flask was charged with sodium propiolate (2-Na, 1.15 g, 12.5 mmol), the appropriate Lindlar catalyst (e.g., 200 mg, 5 wt % Pd(0) on CaCO$_3$ with 3 wt % of PbCO$_3$), hydroquinone (10 mg), and a Teflon-coated stir bar. The appropriate solvent or solvent mixture (40 mL) was added and the solution stirred to dissolve the propiolate. The desired amount of quinoline (0 wt %, 50 wt %, 250 wt %, or 500 wt % of the catalyst, depending on the experiment) was then added via syringe. The flask was sealed with a rubber septum, sealed with parafilm, and evacuated and N$_2$ back-filled three times by means of a needle attached to a double-manifold vacuum line. A plastic 5-mL syringe barrel with the large end cut off was fitted with two He-quality latex balloons (one balloon inserted inside a second balloon), using rubber bands and parafilm. The balloon assembly was purged with nitrogen at least three times. For reactions involving NO nitrogen blanketing atmosphere, the reaction flask was evacuated one more time. The balloon assembly was evacuated, filled with ca. 600-800 mL of hydrogen gas (>2-fold excess), and the syringe barrel fitted with a needle that was then inserted into the septum of the reaction flask. The solution was stirred at room temperature for up to 24 hours, with a small amount (~0.2 mL) of solution removed periodically by syringe. Those aliquots were diluted with 0.4 mL of D$_2$O for analysis by $^1$H and $^{13}$C NMR. For reactions involving nominally 1 atm nitrogen blanketing atmosphere, the syringe barrel of the evacuated/deflated balloon assembly was fitted with a needle that was inserted through the septum of the nitrogen-filled reaction flask. An amount of hydrogen corresponding to a total of 13.3±0.3 mmol (the uncertainty being due to the day-to-day variance in lab temperature and pressure) was syringed into the reaction flask through the septum, using a 100-mL gas-tight syringe equipped with a valve, upon which the balloon was observed to inflate. The solution was stirred at room temperature for about 5 hours. A small amount (~0.2 mL) of solution was removed by syringe and diluted with 0.4 mL of D$_2$O for $^1$H and $^{13}$C NMR at reaction times of 1, 2, and 3 hours. After 5 hours of stirring, (the balloon was completely deflated, indicating that the hydrogen had been consumed), the solution was filtered to remove the catalyst, and washed (to remove quinoline) with 5 mL×3 of CH$_3$OH. The combined washing and reaction solvent was removed by rotary evaporation, and the solid that remained was suspended in 50 mL of ether and stirred for 10 minutes. The solid was then filtered, washed with additional ether (10 mL×3), and dried under vacuum to afford generally 1.10 to 1.15 g of a grey solid. $^{13}$C{$^1$H} NMR (no NOE, see above) was used to determine the final distribution of sodium propiolate (2-Na), sodium acrylate (4), and sodium propionate (5).

It was previously reported that treatment of sodium propiolate in 0.1 M NaOH at 40° C. with hydrogen over Pt-black (L. D. Volkova, et al., *React. Kinet. Catal. Lett.* 1985, 29, 345-351) could produce sodium acrylate. On the basis of this work, the partial reduction of sodium propiolate using the Lindlar catalyst (200 mg per 1.15 g of 2-Na) was herein first investigated in 0.05 M NaOH. However, as shown in Table 1 below, after 24 hours of stirring with a ~2-fold excess of hydrogen, only unreacted sodium propiolate (2-Na) was observed in the NMR spectrum.

the catalyst), which is known to retard the over-reduction reaction. After 1 hour, a distribution ratio of 21:75:4 of 2-Na: 4:5 was observed.

In those first experiments, the reaction flask was placed under partial vacuum (evacuated and nitrogen refilled three times, then evacuated again until the solvent bubbled), and a balloon containing the ca. 2-fold excess hydrogen gas was attached to the flask. To better control the reaction and prevent over-reduction, in subsequent reactions a gas tight syringe was used to deliver close to the stoichiometric quantity of hydrogen required. However, it became apparent that an inert blanketing atmosphere was also needed so that the reactant hydrogen could be consumed without partial vacuum conditions being created in the flask. Hence, all subsequent reactions were performed by first placing the reaction flask under 1 atm of nitrogen, attaching a nitrogen-purged but completely deflated balloon to the flask, and then syringing into the flask a slight molar excess (4-9%) of hydrogen.

Quinoline is customarily added to Lindlar-catalyzed alkyne to alkene reduction reactions at anywhere from 0.05× (5%) to 10× (1000%) on the weight of the catalyst to enhance selectivity for the alkene by, it is believed, decreasing surface interactions of the alkene with the catalyst, and hence retarding reduction of the alkene. As the reaction proceeds, and the starting alkyne is reduced to the alkene, the alkyne concentration decreases and the alkene concentration increases, and competition for hydrogen between the desired alkene product and the starting alkyne increases. Maintaining reaction conditions to retard reaction between hydrogen and the alkene (here the desired sodium acrylate) to give the alkane (sodium propionate) becomes increasingly important toward the end of the reaction, when the alkene to alkyne ratio surpasses 9:1 (90% conversion). However, high concentrations of quinoline also slow the reaction rate to the extent that conversion efficiency is impaired. As a result, it was necessary to determine the optimum amount of quinoline to add.

TABLE 1

Percent distribution of products as a function of solvent[a]

HC≡C—CO$_2$Na (2-Na) $\xrightarrow[\text{solvent, rt}]{\text{excess H}_2\text{ over Lindlar catalyst}}$ H$_2$C=CH—CO$_2$Na (4) + CH$_3$CH$_2$—CO$_2$Na (5)

| Solvent | Other additive | Reaction time (hr) | Distribution[c] 2-Na:4:5 |
|---|---|---|---|
| NaOH (0.05 M) | None | 24 | Unreacted 2-Na only |
| 1:1 0.05 M NaOH:CH$_3$OH | None | 24 | Unreacted 2-Na only |
| deionized H$_2$O | None | 2 | Unreacted 2-Na only |
| CH$_3$OH | None | 1 | 5 only |
| CH$_3$OH | Quinoline[b] | 1 | 21:75:4 |

[a]All reactions used 1.15 g sodium propiolate, 200 mg Acros ® Lindlar catalyst, and 40 mL solvent, and excess hydrogen with no blanketing nitrogen atmosphere present.
[b]Quinoline was added at 500 wt % on the catalyst.
[c]The % distribution is ±1% by $^{13}$C NMR.

Switching to a 1:1 mixture of 0.05 M NaOH:CH$_3$OH also resulted in only unreacted 2-H after 24 hours, and no reaction was also observed when the solvent was deionized water (2 hours). However, when pure CH$_3$OH was used as the solvent, in the presence of a ~2-fold excess of hydrogen, complete over-reduction to sodium propionate (5) was observed within one hour. In this case, the balloon was completely deflated and, due to the excessive consumption of hydrogen, the flask was under negative pressure. This reaction was then repeated with the addition of 1.0 g of quinoline (500% on the weight of Accordingly, a series of reactions were conducted as above (using 4-9% excess hydrogen in nitrogen), in which the amount of quinoline was varied (0 wt %, 50 wt %, 250 wt %, or 500 wt % of the catalyst). A small amount (10 mg, or ca. 0.8 to 1.0% on the starting propiolate) of hydroquinone was added as an inhibitor, though its presence may be unnecessary. Aliquots of the reaction mixture were retrieved at 1, 2, and 3 hours for analysis by proton and carbon NMR. After 5 hours, the reaction mixture was filtered and the solvent removed to obtain the mixture of sodium carboxylates 2-Na, 4, and 5. As can be seen in the results shown in Table 2, below, increasing the concentration of quinoline retards the reaction rate, affording larger amounts of unreacted 2-Na; however the amount of over-reduced product 5 is very similar in all cases. It appears that when the amount of hydrogen gas delivered is only slightly in excess, very little quinoline is required to retard over-reduction: within the margin of uncertainty, the product distribution obtained using no quinoline and 50 wt % quinoline (on the weight of the catalyst) are essentially the same, with only ca. 5% of 5 being formed. However, because a small amount of quinoline did not appear to be harmful to the reaction, subsequent reactions were performed using quinoline at 50 wt % (0.5×).

1-Na being in the range 87-91%. It is unclear at this time whether or not there is a deuterium isotope effect, as the differences in rates and % conversion between 2-Na to 4, and 3-Na to 1-Na appear to be within the uncertainty of the product distribution measurements.

In order to perform the second step of converting 3-Na to 1-Na using deuterium at a more practical (e.g., 10×) scale than the 1.15 g scale employed for the survey hydrogenation reactions, a 3 L-capacity SKC® Flex Foil gas sample bag was used to contain and deliver the deuterium gas to the reaction mixture. A practice hydrogenation reaction of 2-Na at an 11.5 g scale using hydrogen in the Flex Foil bag afforded, after

TABLE 2

Percent distribution of products as a function of quinoline concentration.[a]

$$HC{\equiv}C-CO_2Na \xrightarrow[CH_3OH/quinoline, rt]{H_2/N_2 \text{ mixture over Lindlar catalyst}} H_2C{=}CH-CO_2Na + CH_3CH_2-CO_2Na$$
$$\quad\quad\quad 2\text{-Na} \quad\quad\quad\quad\quad\quad\quad\quad\quad\quad\quad\quad\quad\quad\quad\quad\quad\quad 4 \quad\quad\quad\quad\quad\quad 5$$

| Reaction time (hr)[b] | No quinoline 2-Na:4:5 | 50 wt % quinoline 2-Na:4:5 | 250 wt % quinoline 2-Na:4:5 | 500 wt % quinoline 2-Na:4:5 |
|---|---|---|---|---|
| 1 | 36:60:4 | 37:59:4 | 45:51:4 | 46:49:5 |
| 2 | 17:78:5 | 19:77:4 | 23:73:4 | 20:76:4 |
| 3 | 7:90:3 | 7:90:3 | 16:80:4 | 10:87:3 |
| 5 | 0:95:5 | 0:96:4 | 9:89:2 | 9:88:3 |

[a]Wt % quinoline on Acros ® Lindlar catalyst; 1 atmosphere nitrogen at start; all % distributions are ±1% by $^{13}$C NMR.
[b]Aliquots taken at 1, 2, 3 hours; product isolated at 5 hours (NMR on ca. 100 mg isolated product mixture)

Comparison of Lindlar Catalyst from Different Sources

As the same batch of Lindlar catalyst was employed in all the survey reactions, to test whether the product distribution was dependent on any particular batch of Lindlar catalyst, the reaction was repeated (using conditions of 50 wt % quinoline) with batches of Lindlar catalyst from different sources. As shown in Table 3 below, the results obtained using Lindlar catalyst from three different sources were very similar, within the margin of uncertainty, indicating that similar performance can be expected with Lindlar catalysts from various sources.

TABLE 3

Percent distribution of products as a function of Lindlar catalyst source.[a]

| Reaction time (hr)[b] | Acros ® lot# A017882001 2-Na:4:5 | Aldrich ® Batch# 05812HJ 2-Na:4:5 | AlfaAesar ® lot# K055049 2-Na:4:5 |
|---|---|---|---|
| 1 | 37:59:4 | Not Determined | Not Determined |
| 2 | 19:77:4 | 20:76:4 | 21:74:5 |
| 3 | 7:90:3 | 13:82:5 | 10:85:5 |
| 5 | 0:96:4 | 7:90:3 | 3:94:3 |

[a]All reaction used 50 wt % quinoline on Lindlar catalyst; 1 atmosphere nitrogen at start; all % distributions are ± 1% by $^{13}$C NMR.
[b]Aliquots taken at 1, 2, 3 hours; product isolated at 5 hours (NMR on ca. 100 mg isolated product mixture)

Deuteration Reactions

Having established a set of reaction conditions that could lead to >90% conversion of sodium propiolate to sodium acrylate, experiments were undertaken to prepare sodium acrylate-d$_3$ (1-Na). Trial deuteration reactions of 3-Na at the 1.16 g scale were performed using the same reaction conditions as above, except that CH$_3$OD was used in place of CH$_3$OH, and deuterium instead of hydrogen was syringed into the reaction flask. The results of these trials indicate that the deuteration reaction proceeded in a manner nearly identical to that encountered with hydrogen, with % conversion to stirring for 24 hours, material possessing a 2-Na:4:5 molar distribution of 9%:89%:2% (all values±1%). This reaction was then repeated using 11.6 g (0.125 mole) of 3-Na dissolved in 400 mL CH$_3$OD with 2.0 g Lindlar catalyst, 1.0 mL quinoline, and 0.1 g hydroquinone, in a 1-L reaction flask under nominally 1 atmosphere of nitrogen, as described in detail below.

Scale-Up Preparation of Sodium Acrylate-d$_3$ (1-Na) by Deuteration of Sodium Propiolate-d Over Lindlar Catalyst (5% Pd—CaCO$_3$ w/3% PbCO$_3$) Using 0.5× Quinoline In an exemplary scale-up preparation, sodium propiolate-d (3-Na, 11.6 g, 0.125 mol), Lindlar catalyst (2.0 g, 5 wt % Pd(0) on CaCO$_3$ with 3 wt % of PbCO$_3$), hydroquinone (0.1 g), quinoline (1.0 mL, 8.5 mmol, ~0.5× weight of the catalyst), and CH$_3$OD (400 mL, 324 g, 99.0 atom % D) were combined in a 1 L two-neck round bottom flask with a Teflon-coated stir bar. One neck was fitted with a rubber septum, and the other neck of the flask was fitted with a Pyrex inlet adapter with a 90° hose connection with a short section of Tygon tubing connected to a glass T-connector. One end of the T was connected to a double-manifold vacuum line, and the remaining end of the T was connected using Tygon tubing to the valve-stem of a 3-L capacity SKC® Flex Foil gas sample bag containing nominally 3 L (0.134 mole) of deuterium gas (99.9 atom % D). The valve on the bag was closed, and the Tygon tubing connecting the bag to the T adapter pinched shut with a tubing clamp. The tubing connecting the flask to the vacuum line was not clamped at this time. Using the vacuum line, the flask was evacuated and back-filled with N$_2$ gas three times. The tubing between the T and the vacuum line was then clamped shut, and deuterium gas was admitted to the reaction flask by opening the clamp and the valve on the Flex Foil bag. With the valve open, the solution was stirred at room temperature overnight. At reaction times of 3, 6, and 8 hours, 0.2 mL aliquots were removed via the septum-covered neck using a syringe, as samples for NMR analysis. After about 24 hours, the foil bag was completely flat. The catalyst was filtered off, and the solid was washed with $CH_3OD$ (10 mL×3). The combined solution was placed on a rotary evaporator, and the methanol-d evaporated and recovered. The solid that remained was washed with ether (50 mL×3) and dried under vacuum, to afford 12.01 g of a grey solid. $^{13}C\{^1H\}$ NMR (no NOE) revealed a molar product distribution, based on the ratio of the peak areas of the carbonyl carbons from unreacted sodium propiolate-d (3-Na, 162.9 ppm), sodium acrylate-$d_3$ (1-Na, δ 178.3 ppm), and sodium propionate-$d_5$ (6, over-reduced, δ 188.5 ppm), as 7:90:3 (all values are ±1), resulting in a sodium acrylate-$d_3$ yield of 89%. $^2H$ NMR ($D_2O$) revealed a very similar ratio at 6.3:90.5:3.2. $^{13}C\{^1H\}$ NMR ($D_2O$, TSP): δ 178.3 (s, C=O), 136.0 (t, $D_2C$=CD-, $J_{CD}$=24.4 Hz), 128.8 (p, $D_2C$=CD-, $J_{CD}$=24.4 Hz). $^2H$ NMR ($D_2O$): δ 6.12 (br s, $D_{cis}D_{trans}C$=$CD_{gem}$-), 6.01 (br s, $D_{cis}D_{trans}C$=$CD_{gem}$-), 5.65 (br s, $D_{cis}D_{trans}C$=$CD_{gem}$-), 3.10 (br s, DCC—$CO_2Na$), 2.10 (br s, $CD_3CD_2$-$CO_2Na$), 0.98 (br s, $CD_3CD_2$-$CO_2Na$). Comparison of the $^{13}C$ integrals of the residual signals due to non-deuterated sodium acrylate with deuterated sodium acrylate indicated the sodium acrylate-$d_3$ was >95 atom % D. The recovered $CH_3OD$ was distilled from 3 Å molecular sieves to afford 276 g (85% recovery) of clean material suitable for reuse.

EXAMPLE 3

Experiments Comparing Hydrogen Vs. Deuterium Incorporation During Catalytic Reduction of Sodium Propiolate to Sodium Acrylate A 250-mL round bottom flask was charged with either sodium propiolate (2-Na, 1.15 g, 12.5 mmol) or sodium propiolate-d (3-Na, 1.16 g, 12.5 mmol), Lindlar catalyst (200 mg), hydroquinone (10 mg), and a Teflon-coated stir bar. Methanol or methanol-d (40 mL) was added and the solution stirred to dissolve the propiolate, followed by 0.10 mL of quinoline. The flask was sealed with a rubber septum, sealed with parafilm, and evacuated and $N_2$ back-filled three times by means of a needle attached to a double-manifold vacuum line. A plastic 5-mL syringe barrel with the large end cut off was fitted with two He-quality latex balloons (one balloon inserted inside a second balloon), using rubber bands and parafilm. The balloon assembly was purged with nitrogen at least three times. The syringe barrel of the evacuated/deflated balloon assembly was fitted with a needle that was inserted through the septum of the nitrogen-filled reaction flask. An amount of hydrogen or deuterium corresponding to a total of 13.3±0.3 mmol (the uncertainty being due to the day-to-day variance in lab temperature and pressure) was syringed into the reaction flask through the septum, using a 100-mL gas-tight syringe equipped with a valve, upon which the balloon was observed to inflate. The solution was stirred at room temperature for about 5 hours. A small amount (~0.2 mL) of solution was removed by syringe and diluted with 0.4 mL of $D_2O$ for $^1H$ and $^{13}C$ NMR at reaction times of 1, 2, and 3 hours. After 5 hours of stirring, (the balloon was completely deflated, indicating that the hydrogen or deuterium had been consumed), the solution was filtered to remove the catalyst, and washed (to remove quinoline) with 5 mL×3 of $CH_3OH$ or $CH_3OD$ as appropriate. The volatiles were removed from the combined filtrate and washings by rotary evaporation, and the solid that remained was suspended in 50 mL of ether and stirred for 10 minutes. The solid was then filtered, washed with additional ether (10 mL×3), and dried under vacuum to afford generally 1.10 to 1.15 g of a grey solid. $^{13}C\{^1H\}$ NMR (without NOE enhancement) was used to determine the final distribution of sodium propiolate, sodium acrylate, and sodium propionate, and the degree of deuterium incorporation. Table 4 below shows the effect of using hydrogen or deuterium gas, $CH_3OH$ or $CH_3OD$, and sodium propiolate (2-Na) or sodium propiolate-d (3-Na) on the level of deuterium incorporation in the product sodium acrylate.

TABLE 4

Percent distribution of deuterium in vinyl group as a function of deuterium content in reactants in four different experiments[a]

| | Entry No. | | | |
|---|---|---|---|---|
| | 1 | 2 | 3 | 4 |
| | Conditions | | | |
| | 3-Na/$CH_3OD$/$D_2$ | 3-Na/$CH_3OD$/$H_2$ | 3-Na/$CH_3OH$/$D_2$ | 2-Na/$CH_3OH$/$D_2$ |
| | H/D Distribution in vinyl group of sodium acrylate | | | |
| | % | % | % | % |
| $X_2C$=CY, $X_2$ = $D_2$ (Y either D or H) | 98 | 19 | ND | ND |
| $X_2C$=CY, $X_2$ = DH (Y either D or H) | 2 | 76 | 44 | 33 |
| $X_2C$=CY, $X_2$ = $H_2$ (Y either D or H) | 0 | 5 | 56 | 67 |
| $X_2C$=CY, Y = D ($X_2$ either $D_2$, $H_2$, or DH) | 96 | 19 | 36 | 18 |
| $X_2C$=CY, Y = H ($X_2$ either $D_2$, $H_2$, or DH) | 4 | 81 | 64 | 82 |

[a]Determined by integration of appropriate $^{13}C$ resonances in $^{13}C$ NMR spectra. The uncertainty is approximately ± 5% of the value for entry 1, and ± 10% of the value for entries 2-4.
ND = not detected.

Discussion of Comparative Examples

In entry no. 1 in Table 4, sodium propiolate-d (3-Na) was treated with deuterium gas in $CH_3OD$ to afford sodium acrylate-$d_3$ (1-Na) in which the vinyl group is 98% =$CD_2$ and 2% =CDH in the terminus, and 96% —CD= and 4% —CH= in the internal vinyl carbon. (Note: these values relate to how the D is distributing between the carbon atoms in 1-Na, and does not necessarily relate to the total atom % D in the product mixture.) Changing deuterium to hydrogen (entry no. 2), or replacing CH₃OD with CH₃OH (entry no. 3) resulted in a substantial decrease in the degree of deuteration. Significantly and unexpectedly, when deuterium was replaced with hydrogen (entry no. 2), rather than the expected distribution of 0% =CD₂, 100% =CDH, 0% =CH₂, 0% —CD=, and 100% —CH= (that would be expected from simple addition of H₂ across the DCC-triple bond to from DHC=CH—), the observed distribution was 19% =CD₂, 76% =CDH, 5% =CH₂, 19% —CD=, and 81% —CH=, indicating that H/D scrambling took place during the reduction reaction. Similarly, in the case of entry no. 4, which is the inverse of entry 2 (i.e., 2-Na instead of 3-Na, CH₃OH instead of CH₃OD, and D₂ instead of H₂), the expectation for addition of D₂ across the triple bond was DHC=CD- with a distribution of D in the product acrylate as 0% =CD₂, 100% =CDH, 0% =CH₂, 100% —CD=, and 0% —CH=. However, what was unexpectedly observed was no detectable =CD₂, 33% =CDH, 67% =CH₂, 18% —CD=, and 82% —CH=, indicating that again there was some H/D scrambling and that CH₃OH was likely involved in H transfer. Finally, in entry no. 3, in which CH₃OD was replaced by CH₃OH, interestingly, no =CD₂ was observed, apparently as a result of substantial H/D exchange, resulting in sodium acrylate that was 44% =CDH, 56% =CH₂, 36% —CD=, and 64% —CH=. It was expected that in CH₃OH, some H/D exchange would occur with the deuterated terminal alkyne, but it was surprising that a substantial amount of =CH₂ was observed, indicating that H/D exchange was not only occurring before reduction of the alkyne, but also occurring somehow during the actual catalytic reduction (as was observed in entries 2 and 4 also.) Thus, in order to obtain sodium acrylate with high levels of deuteration and low levels of H/D scrambling, CH₃OD was herein found to be a preferred solvent, in addition to the use of sodium propiolate-d and D₂.

EXAMPLE 4

Method to Convert Sodium Acrylate-d₃ to Acrylic Acid-d₃

2.10 g of solid containing nominally 19.3 mmol of sodium acrylate-d₃, as prepared above, was dissolved in 5 mL H₂O cooled in an ice bath. An aqueous solution of HCl (3N, 7.5 mL) was added. The pH of the resultant solution was ~1. The aqueous solution was extracted with diethyl ether (25 mL×3), and the combined organic layer was dried over anhydrous Na₂SO₄. Hydroquinone (0.5 g) was added to the solution, and the ether fractionally distilled off (oil bath temperature of about 45° C.). The solution that remained was bulb-bulb vacuum transferred to give a colorless liquid of total mass 2.11 g. $^{13}$C{$^1$H} NMR (D₂O): δ 171.0 (C=O from acrylic acid-d₃), 132.8 ("t", D₂C=CD-, J$_{CD}$)=24.8 Hz), 127.9, ("p", D₂C=CD-, J$_{CD}$)=25.2 Hz). Analysis by $^1$H and $^{13}$C NMR revealed the liquid to contain 0.82 g (10.9 mmol, 56%) of acrylic acid-d₃, with the balance being primarily ether and some methanol, and a small amount of (1.4 mmol) of propiolic acid-d from the unreacted sodium propiolate-d. No propionic acid-d₅ was detected. The molar ratio of acrylic acid-d₃ to propiolic acid-d was 88:12. Substitution of D₂O for H₂O and DCl for HCl can afford acrylic acid-d₄.

While there have been shown and described what are at present considered the preferred embodiments of the invention, those skilled in the art may make various changes and modifications which remain within the scope of the invention defined by the appended claims.

What is claimed is:

1. A method for synthesizing a deuterated acrylate of the formula

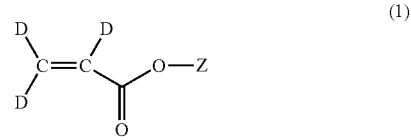

wherein Z is an alkali metal atom or H,
the method comprising:
(i) deuterating a compound of Formula (2) to a compound of Formula (3) by the following reaction pathway conducted in the presence of a base and D₂O:

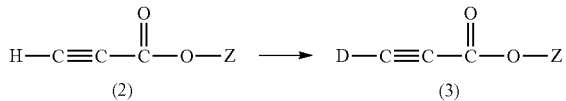

and
(ii) reductively deuterating the compound of Formula (3) in a reaction solvent in the presence of deuterium gas and a palladium-containing catalyst to afford the deuterated acrylate of the Formula (1).

2. The method of claim 1, wherein Z is an alkali metal.

3. The method of claim 1, wherein the base in step (i) is non-protic.

4. The method of claim 3, wherein the non-protic base is a carbonate salt.

5. The method of claim 1, wherein step (i) is practiced by removal of D₂O and its proton-exchanged forms after an initial reaction to convert the compound of Formula (2) to the compound of Formula (3), followed by addition of fresh D₂O and further deuterating the compound of Formula (2) to the compound of Formula (3).

6. The method of claim 1, wherein the reaction solvent in step (ii) is a deuterated alcohol in which at least the protic hydrogen of the deuterated alcohol is replaced with a deuterium atom.

7. The method of claim 6, wherein the deuterated alcohol is deuterated methanol.

8. The method of claim 1, wherein the deuterium gas in step (ii) is used in an excess of 5-15% in an inert gas.

9. The method of claim 1, wherein the deuterium gas in step (ii) is used in an excess of 7-10% in an inert gas.

10. The method of claim 1, wherein the palladium-containing catalyst is a Lindlar catalyst comprised of Pd(0) on calcium carbonate or barium sulfate along with deactivators comprised of lead additive and organic inhibitor.

11. The method of claim 10, wherein said organic inhibitor is selected from nitrogen-containing and sulfur-containing organic compounds.

12. The method of claim 11, wherein said organic inhibitor is selected from quinoline and 2,2'-(ethylenedithio)diethanol.

13. The method of claim 10, wherein said Lindlar catalyst is included in an amount of 5-25 wt % by weight of the compound of Formula (3).

14. The method of claim 10, wherein said quinoline is included in an amount of up to 50% by weight of the catalyst.

15. The method of claim 10, wherein the Pd(0) is in an amount of about 4-6 wt % by weight of the Lindlar catalyst.

16. The method of claim 10, wherein the lead additive is used in an amount of 2-5 wt % by weight of the Lindlar catalyst.

17. The method of claim 1, wherein step (ii) is conducted in the presence of a radical polymerization inhibitor.

18. The method of claim 17, wherein said radical polymerization inhibitor is included in an amount of up to 2 wt % by weight of the compound of Formula (3).

19. The method of claim 17, wherein said radical polymerization inhibitor is hydroquinone or 2,6-di-tert-butyl-4-methylphenol.

20. The method of claim 1, wherein Z is an alkali metal atom, and the method further comprises protonating the compound of Formula (1) to make Z a hydrogen or deuterium atom.

21. The method of claim 1, wherein the compound of Formula (1) is obtained in a yield of at least 80%.

22. The method of claim 1, wherein the compound of Formula (1) is obtained in a yield of at least 85%.

23. The method of claim 1, wherein the compound of Formula (1) has a level of deuteration of at least 90 atom % D.

24. The method of claim 1, wherein the compound of Formula (1) has a level of deuteration of at least 95 atom % D.

25. The method of claim 1, wherein side reaction byproducts resulting from step (ii), including unreacted compound of Formula (3) and sodium propionate, are present in an amount of no more than 10 mole % with respect to total product resulting from the reaction of step (ii).

26. The method of claim 1, wherein side reaction byproducts resulting from step (ii), including unreacted compound of Formula (3) and sodium propionate, are present in an amount of no more than 7 mole % with respect to total product resulting from the reaction of step (ii).

* * * * *